United States Patent
Dong (10) Patent No.: US 9,420,980 B2
(45) Date of Patent: Aug. 23, 2016

(54) IMAGING SYSTEM ROTATING GANTRY AND SUBJECT SUPPORT MOTION CONTROL

(71) Applicant: KONINKLIJKE PHILIPS ELECTRONICS N.V., Eindhoven (NL)

(72) Inventor: Shufang Dong, Mayfield Heights, OH (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 84 days.

(21) Appl. No.: 14/346,743

(22) PCT Filed: Sep. 25, 2012

(86) PCT No.: PCT/IB2012/055092
§ 371 (c)(1),
(2) Date: Mar. 24, 2014

(87) PCT Pub. No.: WO2013/046117
PCT Pub. Date: Apr. 4, 2013

(65) Prior Publication Data
US 2014/0241491 A1    Aug. 28, 2014

Related U.S. Application Data

(60) Provisional application No. 61/539,193, filed on Sep. 26, 2011.

(51) Int. Cl.
A61B 6/04     (2006.01)
A61B 6/03     (2006.01)
A61B 6/00     (2006.01)

(52) U.S. Cl.
CPC .............. *A61B 6/0457* (2013.01); *A61B 6/035* (2013.01); *A61B 6/547* (2013.01); *A61B 6/4476* (2013.01); *A61B 6/56* (2013.01)

(58) Field of Classification Search
CPC ........................................................ A61B 6/56
USPC ...................................................... 378/4–20
See application file for complete search history.

(56) References Cited

U.S. PATENT DOCUMENTS

| 6,507,639 B1 | 1/2003 | Popescu |
| 6,751,688 B1 | 6/2004 | El-Demerdash et al. |
| 8,208,699 B2 * | 6/2012 | Hay et al. ...................... 382/128 |
| 2002/0039403 A1 | 4/2002 | Oota |
| 2002/0054659 A1 | 5/2002 | Okumura et al. |
| 2003/0068005 A1 | 4/2003 | Yamazaki |

(Continued)

OTHER PUBLICATIONS

Baldor "Real-Time Ethernet Motion Solutions"; 2009; retrieved on Oct. 6, 2011 from the Internet www.Baldormotion.com 48 pages. Baldor Electric Company, Fort Smith, Arkansas, USA.

(Continued)

*Primary Examiner* — Hoon Song (57) ABSTRACT

An imaging system (300) includes a rotating gantry (302) configured to rotate about an examination region (306) about a z-axis (308), a subject support (322), including a tabletop (324) configured to horizontally translate along the z-axis into and out of the examination region, a communications network (342) shared by the rotating gantry and the subject support, and a master motion controller (344) configured to control both rotational motion of the rotating gantry and translational motion of the tabletop over the communications network.

22 Claims, 4 Drawing Sheets

(56) References Cited

U.S. PATENT DOCUMENTS

| | | | | |
|---|---|---|---|---|
| 2003/0091157 | A1* | 5/2003 | Nakanishi | A61B 6/032 378/205 |
| 2004/0065465 | A1 | 4/2004 | Chappo et al. | |
| 2005/0259782 | A1* | 11/2005 | Kasuya | 378/15 |
| 2006/0276775 | A1* | 12/2006 | Rosenberg et al. | 606/1 |
| 2007/0105922 | A1 | 5/2007 | Buettelmann et al. | |
| 2007/0171104 | A1 | 7/2007 | Kanayama | |
| 2007/0195922 | A1* | 8/2007 | Mackie et al. | 378/4 |
| 2008/0159470 | A1* | 7/2008 | Sadotomo et al. | 378/15 |
| 2009/0276093 | A1 | 11/2009 | Bird-Radolovic | |
| 2010/0100198 | A1* | 4/2010 | Hermann | 700/11 |
| 2010/0118896 | A1 | 5/2010 | Grottel et al. | |

OTHER PUBLICATIONS

Newport, D. F., et al.; QuickSilver: A Flexible, Extensible, and High-Speed Architecture for Multi-Modality Imaging; 2006; IEEE Trans. on Nuclear Science; M08-1; 2333-2334.

* cited by examiner

FIGURE 5

IMAGING SYSTEM ROTATING GANTRY AND SUBJECT SUPPORT MOTION CONTROL

CROSS REFERENCE TO RELATED APPLICATIONS

This application is a national filing of PCT application Serial No. PCT/IB2012/055092, filed Sep. 25, 2012, published as WO 2013/046117 A1 on Apr. 4, 2013, which claims the benefit of U.S. provisional application Ser. No. 61/539,193 filed Sep. 26, 2011, which is incorporated herein by reference.

The following generally relates to an imaging system and more particularly to rotating gantry and subject support motion control of the imaging system through a central master motion controller, and is described with particular application to computed tomography (CT); however, the following is also amenable to rotating gantry and subject support motion control of other the imaging systems.

Figure 1:
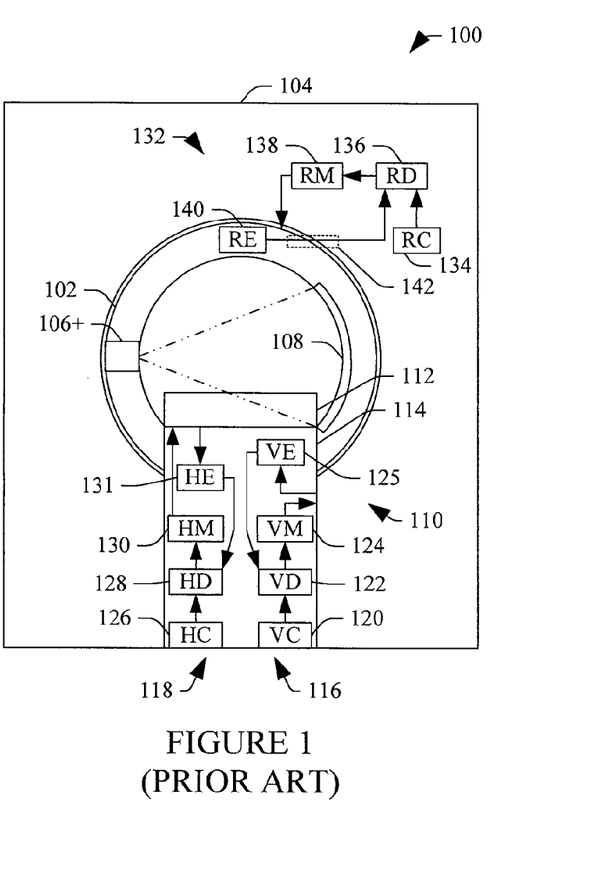
FIG. 1 schematically illustrates a front view of an example prior art CT scanner having dedicated rotating gantry, subject support horizontal tabletop, and subject support vertical base controllers and a dedicated hard-wired channel for the rotor encoder from the rotating gantry to the stationary gantry.
Figure 2:
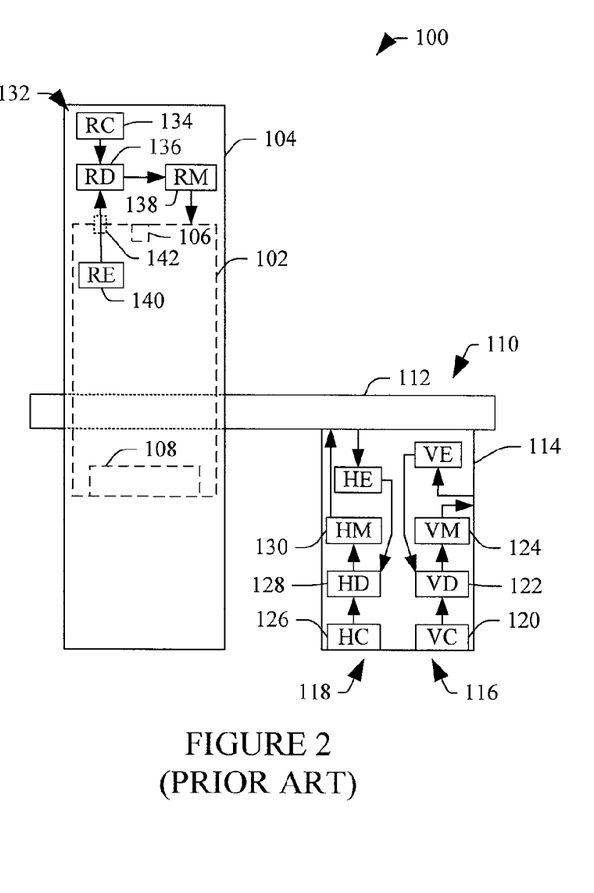
FIG. 2 schematically illustrates a side view of the example prior art CT scanner of FIG. 1.

FIGS. 1 and 2 show an example computed tomography (CT) scanner 100. FIG. 1 shows a front view of the scanner 100, and FIG. 2 shows a side view of the scanner 100. The CT scanner 100 includes a rotating gantry 102 rotatably mounted to a stationary gantry 104. The rotating gantry 102 supports an x-ray tube 106 and a detector array 108, which is located opposite the x-ray tube 106, across an examination region. A subject support 110 is configured to move vertically and horizontally to load a subject or object, position the subject or object in the examination region, and unload the subject or object. The rotating gantry 102 and thus the x-ray tube 106 rotate around the examination region about a longitudinal or z-axis. The x-ray tube 106 emits radiation that traverses the examination region and a portion of a subject or object disposed therein via the subject support 110. The detector array 108 detects the radiation traversing the examination region and generates a signal indicative of the detected radiation.

The subject support 110 includes a tabletop 112, a base 114, a dedicated vertical drive system 116, and a dedicated horizontal drive system 118. The vertical drive system 118 includes a vertical controller 120, a vertical drive 122, a vertical motor 124 and a vertical encoder 125, and controls vertical motion of the base 114. Generally, the vertical controller 120 stores a vertical motion profile and controls the vertical drive 122, which, based on feedback from the vertical encoder 125, controls the vertical motor 124, which vertically moves the base 114. The horizontal drive system 118 includes a horizontal controller 126, a horizontal drive 128, a horizontal motor 130 and a horizontal encoder 131, and controls horizontal motion of the tabletop 112. Generally, the horizontal controller 126 stores a horizontal motion profile and controls the horizontal drive 128, which, based on feedback from the horizontal encoder 131, controls the horizontal motor 130, which horizontally moves the tabletop 112.

The rotating and stationary gantries 102 and 104 include a dedicated rotor drive system 132. The stationary gantry 104 includes a first portion of the rotor drive system 132, which includes a rotor controller 134, a rotor drive 136 and a rotor motor 138, and the rotating gantry 104 includes a second portion of the rotor drive system 132, which includes a rotor encoder 140. Generally, the rotor controller 134 stores a rotational motion profile and controls the rotor drive 136, which, based on positional feedback from the rotor encoder 140, controls the rotor motor 138, which rotates the rotating gantry 102. The feedback from the rotor encoder 140 to the rotor drive 136 is conveyed via a dedicated hard-wired channel such as channel 142 over a slip ring from the rotating gantry 102 to the stationary gantry 104. Additionally or alternatively, an encoder (not included in this embodiment) located in the stationary gantry 104 at the vertical motor 124 can be used to provide rotating gantry position feedback to the rotor controller 134.

In the above implementation, each of the rotating drive system 132, the vertical drive system 116 and the horizontal drive system 118 includes a dedicated motion controller (i.e., the rotor controller 134, the vertical controller 120 and the horizontal controller 126) and the rotating drive system 132 includes a dedicated hard-wired channel such as channel 142. Unfortunately, each of the dedicated motion controllers 132, 116 and 118 and the dedicated hard-wired channel 142 adds cost to the overall system 100 and consumes space. As such, there is an unresolved need for another approach to control the motion of at least the rotating gantry 102, the tabletop 114, and the base 116 of a CT scanner such as the scanner 100.

Aspects described herein address the above-referenced problems and others.

In one aspect, an imaging system includes a rotating gantry configured to rotate about an examination region about a z-axis, a subject support, including a tabletop configured to horizontally translate along the z-axis into and out of the examination region, a communications network shared by the rotating gantry and the subject support, and a master motion controller configured to control both rotational motion of the rotating gantry and translational motion of the tabletop over the communications network.

In another aspect, a method includes polling, via a master motion controller configured to control a motion of a rotating gantry and a subject support over a communications network, one of a rotating gantry encoder or a subject support encoder respectively for rotating gantry or subject support position information over the communications network and receiving the rotating gantry or subject support position information. The method further includes comparing the received rotating gantry or subject support position information with a corresponding desired position of the rotating gantry or subject support. The method further includes controlling, via the master motion controller, a motion of the one of the rotating gantry or the subject support based on a result of the comparing.

In another aspect, an imaging system includes a stationary gantry and a rotating gantry, rotatably supported by the stationary gantry, and configured to rotate about an examination region about a z-axis. The imaging system further includes a radiation source, configured to emit ionizing radiation and supported by the rotating gantry, and a detector array, configured to detect the ionizing radiation and generate projection data indicative thereof. The imaging system further includes a subject support having a base configured to vertically translate along a y-axis and a tabletop, slideably affixed to the base, and configured to horizontally translate along the z-axis into and out of the examination region. The imaging system further includes a communications network shared by the rotating gantry and the subject support. The imaging system further includes a master motion controller (344) configured to control rotational motion of the rotating gantry and translational motion of the subject support over the communications network.

The invention may take form in various components and arrangements of components, and in various steps and arrangements of steps. The drawings are only for purposes of illustrating the preferred embodiments and are not to be construed as limiting the invention.

Figure 3:
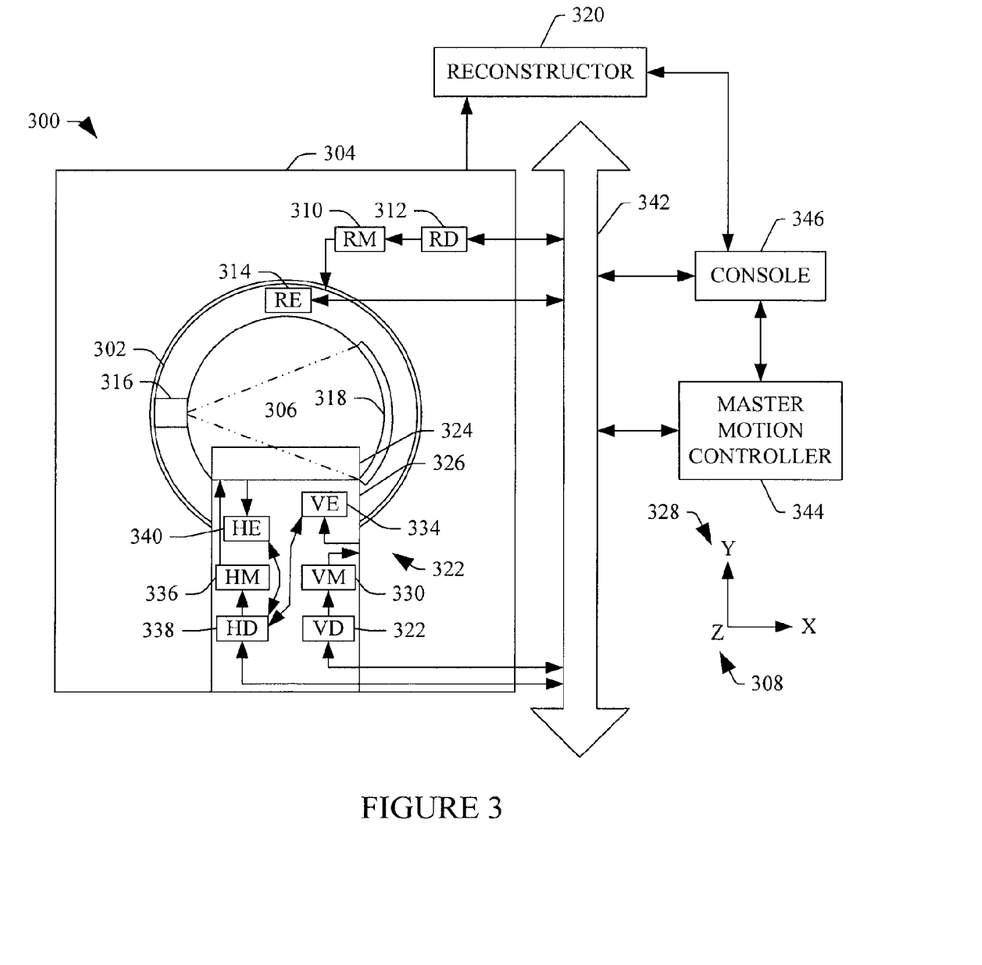
FIG. 3 schematically illustrates an example imaging system including centralized motion control of the rotating gantry, the subject support horizontal tabletop, and the subject support vertical base.

Initially referring to FIG. 3, an imaging system 300, such as a computed tomography (CT) scanner, is schematically illustrated. The imaging system 300 includes a stationary gantry 302 and a rotating gantry (rotor) 304, which is rotatably supported by the stationary gantry 302 via a ball, air, etc. bearing or the like. The rotating gantry 304 rotates around an examination region 306 about a longitudinal or z-axis 308. A rotor motor 310 rotates the rotating gantry 304, directly or through another component such as a belt, a chain, gears, or the like. A rotor drive 312 controls the rotor motor 310 based on rotating gantry position feedback. A rotor encoder 314, located on the rotating gantry 302, determines an angular rotational position of the rotating gantry 304. The rotor encoder 314 conveys the position information from the rotating gantry 304 to the stationary gantry 302 over a slip ring or the like.

A radiation source 316, such as an x-ray tube, is supported by and rotates with the rotating gantry 304 around the examination region 306 about the longitudinal or z-axis 308. The radiation source 316 emits radiation that is collimated by a collimator to produce a generally fan, wedge, or cone shaped radiation beam that traverses the examination region 306. A detector array 318 subtends an angular arc opposite the examination region 306 relative to the radiation source 316. The detector array 118 detects radiation that traverses the examination region 306 and generates a signal indicative thereof. A reconstructor 320 reconstructs the signal and generates volumetric image data indicative of the examination region 306.

A subject support 322, such as a couch, supports an object or subject in the examination region 306. The subject support 322 is configured to move in the y and/or z directions 328 or 308 to position the subject or object in the examination region 306 before, during and/or after an imaging examination. The subject support 322 includes a tabletop 324 and a base 326. The tabletop 324 is configured to provide horizontal (z direction 308) motion, and the base 326 is configured to provide vertical (y direction 328) motion. A horizontal motor 336 moves the tabletop 324, a horizontal drive 338 drives the horizontal motor 336 based on horizontal positional feedback, and a horizontal encoder 340 determines a horizontal position of the tabletop 324 and conveys this information to the horizontal drive 338. A vertical motor 330 moves the base 326, a vertical drive 322 drives the vertical motor 330 based on vertical positional feedback, and a vertical encoder 334 determines a vertical position of the base 304 and conveys this information to the vertical drive 322.

As described in greater detail below, the system 300 further includes a communication network 342, which is shared by the rotor encoder 314, the rotor drive 312, the vertical drive 322, the horizontal drive 338, and a centralized master motion controller 344, which is configured to control the rotor drive 312, the vertical drive 322 and/or the horizontal drive 338, over the communication network 342, respectively based on position feedback from the rotor encoder 314, the vertical encoder 334 and the horizontal encoder 340. In one non-limiting instance, such a configuration mitigates multiple different controllers for each of the rotating gantry 302, the tabletop 324 and the base 326, and a dedicated hard-wired data channel between the rotating gantry 302 and the stationary gantry 304 for conveying rotating gantry position feedback. In one instance, this may decrease overall system complexity and/or cost.

A general purpose computing system serves as an operator console 346, and includes an output device such as a display and an input device such as a keyboard, mouse, and/or the like. Software resident on the console 346 allows an operator to control the operation of the system 300.

Figure 4:
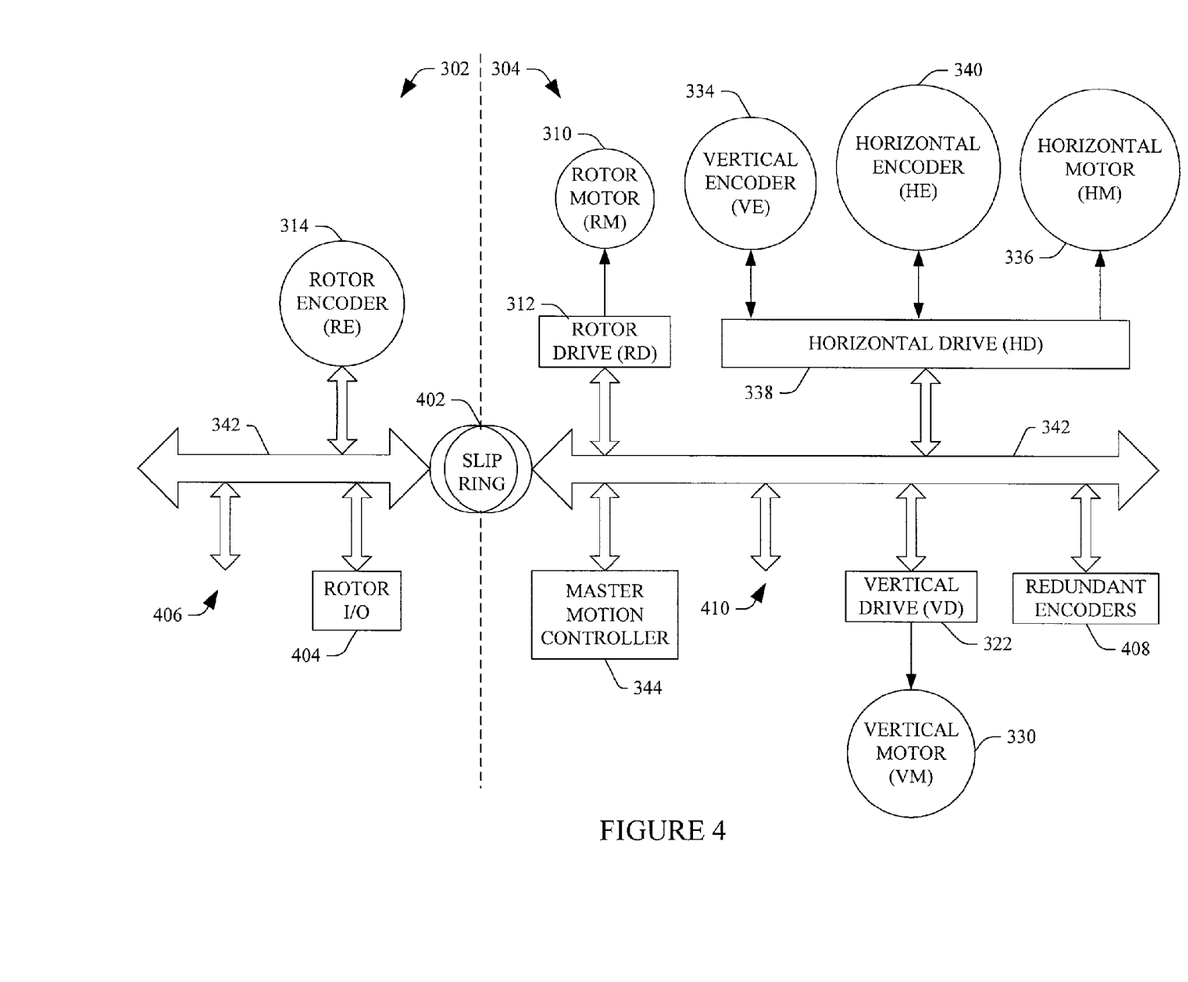
FIG. 4 schematically illustrates an example architecture of the centralized motion control.

FIG. 4 schematically illustrates an example in which the centralized master motion controller 344 controls the rotor drive 312, the vertical drive 322, and the horizontal drive 338 over the control communication network 342.

In this example, the communication network 342 includes a fast, reliable and deterministic network that includes time stamping. Suitable networks include, but are not limited to EtherCAT or CANopen. For sake of brevity and explanatory purposes, the following is discussed in connection with CANopen. CANopen is an application layer network protocol based on the data link layer and physical layer of CAN (control area network) bus. Generally, CANopen is a lower cost slave/master node implementation, with wide availability of hardware and software, suitable bandwidth for CT control and signal data flow, and deterministic response.

In FIG. 4, the communication network 342 extends between the rotating gantry 302 and the stationary gantry 304 via a slip ring 402. On the rotating gantry 302 side, the rotor encoder 314 is directly in electrical communication with the control communication network 342. On the stationary gantry 304 side, the master motion controller 344 is directly in electrical communication with the control communication network 342 and the rotor drive 312 is directly in electrical communication with the control communication network 342 and the rotor motor 310.

In this manner, the master motion controller 344 can poll the encoder 314 for rotating gantry position information (feedback) based on a predetermined polling frequency, determine a synchronized control command as motor speed or frequency based thereon, and convey the control command to the rotor drive 312 to command the rotor drive 312 to drive the rotor motor 310, based on the feedback. By sharing the control communication network 342, the network based rotor feedback and command channel mitigates the dedicated hard-wired rotor encoder channel 142 shown in FIGS. 1 and 2. In addition, the rotor drive 312 does not need encoder module functionality and thus a less expensive rotor drive, without such functionality, can be employed, and, therefore, overall system cost can be reduced.

The rotating gantry 302 side also includes other rotating gantry input/output (rotor I/O) 404 directly in electrical communication with the control communication network 342. The rotor I/O 404 shares the control communication network 342 with the rotor encoder 314. The rotor I/O 404 includes, but is not limited to, I/O corresponding to the radiation source 316, I/O corresponding to the detector array 318, and/or I/O corresponding to other components of the rotating gantry 302. In another embodiment, the rotor I/O 404 is omitted. The control communication network 342 may also include at least one open port, as shown at 406, on the rotating gantry 302 side.

On the stationary gantry 304 side, the horizontal drive 338 and the vertical drive 322 are directly in electrical communication with the control communication network 342. The vertical encoder 334, the horizontal encoder 340 and the horizontal motor 336 are all connected to ports of the horizontal drive 338, which, in the illustrated embodiment, is a more sophisticated multi-port drive designed for either DC and/or AC servo motor control. By using the port of the horizontal drive 338 to communicate with the vertical encoder 334, the vertical drive 322 does not need encoder module functionality and, thus, a less expensive vertical drive, without such functionality, can be employed, and, therefore, overall system cost can be reduced. However, the vertical encoder 334 can alternatively be connected to the vertical drive 322.

Likewise, the master motion controller 344 can poll the horizontal and vertical encoders 334 and 340 for tabletop horizontal and base vertical position information (feedback) based on a predetermined polling frequency, determine synchronized control commands, and convey the control commands to the horizontal and vertical drives 338 and 322 to command the horizontal and vertical drives 338 and 322 to drive the horizontal and vertical motors 336 and 330 to horizontal and vertical move the tabletop 324 and base 326.

In the illustrated embodiment, the stationary gantry 304 side also includes redundant encoders 408 directly in electrical communication with the control communication network 342. In another embodiment, redundant encoders 408 are omitted. The control communication network 342 may also include at least one open port, as shown at 410, on the stationary gantry 304 side.

With the configuration of FIG. 4, the synchronized CANopen process data object receiving and transmitting, synchronized data processing and control calculation in CANopen master can be used to catch the network data updating rate so that the physical locations of feedback encoders and electric drives can be separated and selectively placed on the CAN network, directly or indirectly.

The following illustrates an example switching control law for rotating gantry and subject support positioning.

Low cost, AC, variable frequency drives typically operate in speed control mode either in volts/Hz or sensorless vector control. Such open loop speed control mode requires a speed reference input from the centralized motion controller 344. With the speed reference, the output frequency and voltage to motor can be regulated to achieve a set speed, without encoder or tachometer feedback.

The speed response of drives can be modeled as a first order low pass filter as shown in EQUATION 1:

$$\frac{\lambda}{p+\lambda},\qquad\text{EQUATION 1}$$

where $\lambda$ is the filter bandwidth and p is the Laplace variable. EQUATION 1 considers the belt reducer or gear reducer dynamics, and variable frequency drive tuning and motor characteristics.

The system can be described as shown in EQUATION 2:

$$\ddot{x}=\lambda\dot{x}+\lambda u,\qquad\text{EQUATION 2}$$

where x is the actual position, $\dot{x}$ is the actual velocity, $\ddot{x}$ is the actual acceleration, and u is the speed reference input.

The position tracking error can be described as shown in EQUATION 3:

$$\tilde{x}=x_d-x,\qquad\text{EQUATION 3}$$

where $x_d$ is the desired positioning profile.

From EQUATIONS 1-3, a feedback switching control and feed-forward control law can be determined as shown in EQUATION 4:

$$u=\dot{x}_d+\frac{\ddot{x}_d}{\lambda}+\eta\cdot\text{sgn}(s),\qquad\text{EQUATION 4}$$

where $\dot{x}_d$, as the speed feed-forward portion, is the desired speed of positioning profile, $\ddot{x}_d$, as the acceleration feed-forward portion, is the desired acceleration of positioning profile, $\eta$ is the switching feedback control effort based on the combined value of position and speed tracking error s, sgn(s) is the sign of the sliding surface variable s, and s is a sliding surface variable defined as shown in EQUATION 5:

$$s=\left(\frac{d}{dt}+\lambda\right)\tilde{x},\qquad\text{EQUATION 5}$$

where, as s converges to zero, the tracking error $\tilde{x}$ converges to zero, which means the actual position will follow the desired rotating gantry 302 or subject support base 326 vertical position.

The positioning control system will be stable upon satisfaction of $\eta>\alpha/\lambda$, where $\alpha$ describes the total absolute model uncertainty quantity, including unmolded high frequency system dynamics and disturbance such as the friction level variation.

In theory, the larger of the value of $\eta$, the larger control efforts u, the faster and smaller of the positioning tracking error will be in the steady state. In reality, too big control effort will require a big electric drive and motor, and will arouse system resonance and result distorted response.

The derivation of the above switching control law is based on the assumption of a continuous control system, while the motion control system in reality will be a sampled discrete and digital system. For sampled motion control system, the amount of switching control effort and switching frequency can be controlled so that an acceptable position tracking accuracy and response rate is achieved.

For an AC variable frequency drive, $\eta$ can be mapped to the rated slip frequency of the motor to get maximum acceleration and deceleration level from the system. To smooth the control effort when the system response is close to the sliding surface, the switching control law can be estimated as shown in EQUATION 6:

$$u=\dot{x}_d+\frac{\ddot{x}_d}{\lambda}+\eta\cdot\begin{cases}\text{sgn}(s) & f|s|>W_S\\ \dfrac{s}{W} & \text{if }|s|<W_s,\end{cases}\qquad\text{EQUATION 6}$$

where $W_s$ is the depth of the boundary layer of the sliding surface variable s, which directly reflects the acceptable position tracking accuracy.

Figure 5:
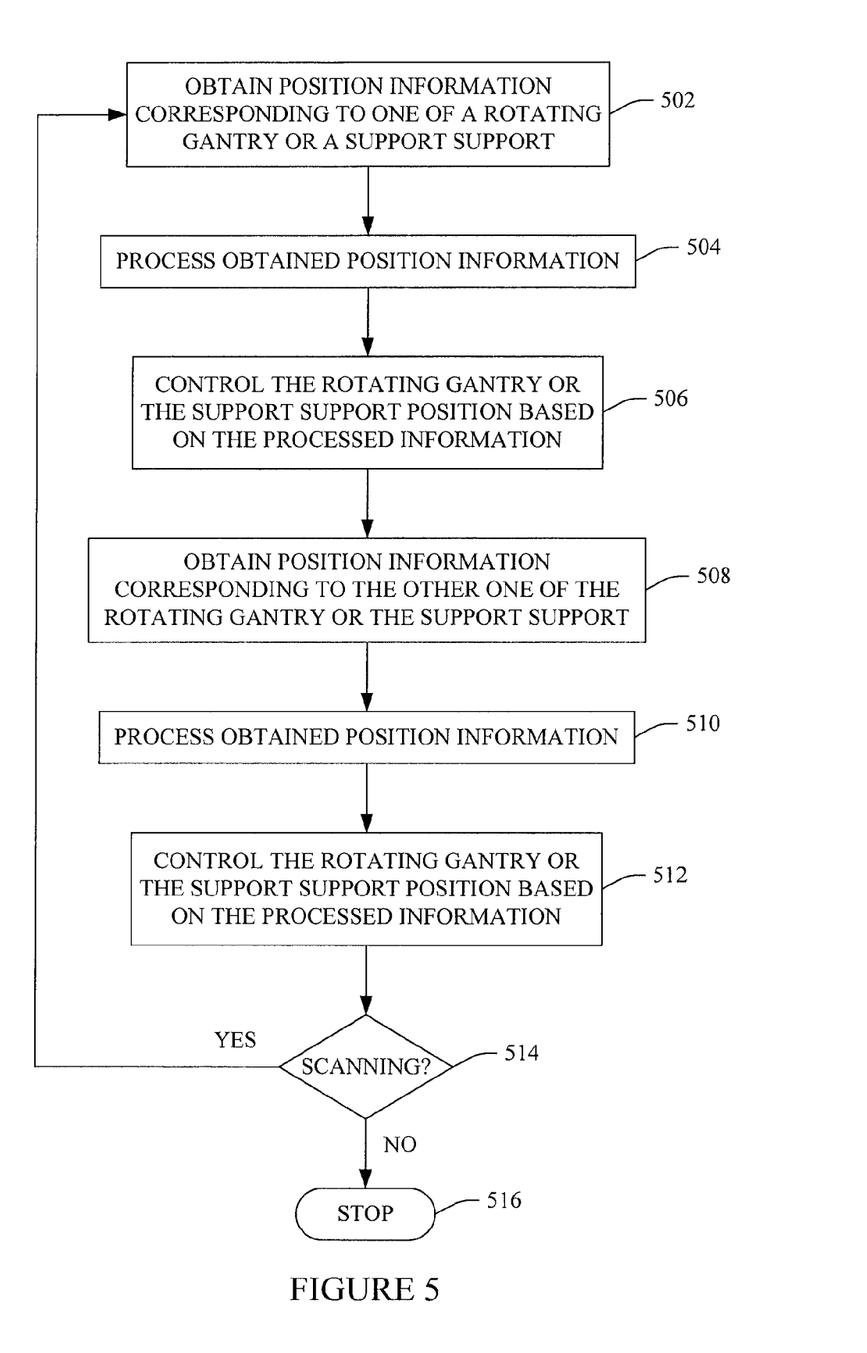
FIG. 5 illustrates a method of controlling motion of the rotating gantry, the subject support horizontal tabletop, and the subject support vertical base based on centralized motion control.

FIG. 5 illustrates a method of controlling rotating gantry and tabletop motion during scanning using a single master motion controller and a shared network.

It is to be appreciated that the ordering of the acts in the methods described herein is not limiting. As such, other orderings are contemplated herein. In addition, one or more acts may be omitted and/or one or more additional acts may be included.

At 502, position information corresponding to one of a rotating gantry rotational position or a subject support (tabletop ad/or base) translational position is obtained from a corresponding encoder during an imaging procedure by a master motion controller over a shared network. In one instance, this is achieved by the master motion controller polling the encoder over the shared network.

At 504, the obtained position information is processed by the master motion controller.

At 506, a motion drive of the one of the rotating gantry or the subject support is controlled with the master motion controller, based on the obtained rotational position or translational position and on a rotational position of interest or translational position of interest.

At 508, position information corresponding to the other of the rotating gantry rotational position or the subject support translational position is obtained from a corresponding encoder during the imaging procedure by the master motion controller over the shared network. Likewise, this is achieved by the master motion controller polling the encoder over the shared network.

At 510, the obtained position information is processed by the master motion controller.

At 512, a motion drive of the other of the rotating gantry or the subject support is controlled with the master motion controller, based on the obtained rotational position or translational position and on the rotational position of interest or the translational position of interest.

At 514, if the imaging procedure is still being performed, then acts 502 to 512 are repeated. If not, then at 516, motion control during scanning is stopped.

Although the above is described in connection with scanning, a similar approach can be used before and/or after scanning for the gantry rotational position, the tabletop horizontal position, and the base vertical position.

The above may be implemented via one or more processors executing one or more computer readable instructions encoded or embodied on computer readable storage medium such as physical memory which causes the one or more processors to carry out the various acts and/or other functions and/or acts. Additionally or alternatively, the one or more processors can execute instructions carried by transitory medium such as a signal or carrier wave.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. An imaging system, comprising:
   a rotating gantry configured to rotate about an examination region about a z-axis;
   a subject support, including a tabletop configured to horizontally translate along the z-axis into and out of the examination region;
   a communications network including a bus extended through a slip ring and shared by the rotating gantry and the subject support; and
   a master motion controller configured to control both rotational motion of the rotating gantry and translational motion of the tabletop over the bus of the communications network.

2. The imaging system of claim 1, wherein the master motion controller is configured to alternately poll at a predetermined frequency for a rotational position of the rotating gantry and a translational position of the tabletop over the bus of the communications network.

3. The imaging system of claim 1, further comprising:
   a rotating gantry motor configured to rotate the rotating gantry;
   a rotating gantry drive configured to drive the rotating gantry motor; and
   a rotating gantry encoder, supported by the rotating gantry, configured to determine a first signal indicative of a rotational position of the rotating gantry,
   wherein the rotating gantry encoder conveys the first signal to the master motion controller over the bus of the communications network via the slip ring, and the master motion controller controls, based at least on the first signal, the rotating gantry drive to controllably rotate the rotating gantry.

4. The imaging system of claim 1, further comprising:
   a subject support horizontal motor configured to translate the tabletop;
   a subject support horizontal drive configured to drive the subject support horizontal motor; and
   a subject support horizontal encoder configured to determine a second signal indicative of a horizontal position of the tabletop,
   wherein the subject support horizontal encoder conveys the second signal to the master motion controller over the bus of the communications network, and the master motion controller controls, based at least on the second signal, the subject support horizontal drive to controllably horizontally translate the tabletop.

5. The imaging system of claim 4 the subject support, further comprising:
   a base, to which the tabletop is slideably affixed, configured to vertically translate the tabletop along a y-axis, wherein the base also shares the bus of the communications network, and the master motion controller is configured to additionally control the base over the bus of the communications network.

6. The imaging system of claim 5, further comprising:
   a subject support vertical motor configured to translate the base;
   a subject support vertical drive configured to drive the subject support horizontal motor; and
   a subject support vertical encoder configured to determine a third signal indicative of a vertical position of the tabletop,
   wherein the subject support vertical encoder conveys the third signal to the master motion controller over the bus of the communications network, and the master motion controller controls, based at least on the third signal, the subject support vertical drive to controllably vertically translate the tabletop.

7. The imaging system of claim 4, wherein the subject support vertical encoder, the subject support horizontal encoder, and the subject support horizontal motor interface with the bus of the communications network through ports of the subject support horizontal drive, and the subject support vertical motor interfaces with the bus of the communications network through a port of the subject support vertical drive.

8. The imaging system of claim 4, wherein the subject support horizontal encoder and the subject support horizontal motor interface with the bus of the communications network through ports of the subject support horizontal drive, and the subject support vertical encoder and the subject support vertical motor interface with the bus of the communications network through ports of the subject support vertical drive.

9. The imaging system of claim 1, wherein the communications network includes a CANopen based network.

10. The imaging system of claim 1, wherein the communications network includes an EtherCAT based network.

11. The imaging system of claim 1, further comprising:
a stationary gantry configured to rotatably support the rotating gantry;
a slip ring between the rotating gantry and the stationary gantry; and
wherein the bus of the communications network extends between rotating gantry and the stationary gantry via the slip ring and includes ports on the rotating gantry and the stationary gantry.

12. The imaging system of claim 1, further comprising:
at least one of a radiation source or a detector array supported by the rotating gantry, wherein the at least one of the radiation source or the detector array communicates with a stationary gantry over the bus of the communications network.

13. The imaging system of claim 1, further comprising:
a redundant encoder of at least one of the rotating gantry, the tabletop, or a base of a radiation source, wherein the redundant encoder communicates over the bus of the communications network; and
wherein the bus of the communications network includes an open port disposed on the rotating gantry.

14. A method, comprising:
polling, via a master motion controller configured to control a motion of a rotating gantry and a subject support over a bus of a communications network extended by a slip ring to span the rotating gantry and subject support, one of a rotating gantry encoder or a subject support encoder respectively for rotating gantry or subject support position information over the bus of the communications network and receiving the rotating gantry or subject support position information;
comparing the received rotating gantry or subject support position information with a corresponding desired position of the rotating gantry or subject support; and
controlling, via the master motion controller, a motion of the one of the rotating gantry or the subject support based on a result of the comparing.

15. The method of claim 14, further comprising:
polling at a pre-determined frequency, via the master motion controller, the other of the one of the rotating gantry encoder or the subject support encoder for position information over the bus of the communications network through the slip ring and receiving the position information;
comparing the received position information with a corresponding desired position; and
controlling, via the master motion controller, a motion of the other of the one of the rotating gantry or the subject support based on a result of the comparing.

16. The method of claim 14, wherein the master motion controller alternately polls the rotating gantry and the subject support encoders at a predetermined polling frequency.

17. The method of claim 14, wherein the rotating gantry encoder is located on a rotating gantry and the master motion controller is located on a stationary gantry, and the rotating gantry and the stationary gantry communicate over a slip ring via the bus of the communications network.

18. The method of claim 14, wherein the subject support motion includes horizontal motion of a tabletop of the subject support.

19. The method of claim 14, wherein the subject support motion includes vertical motion of a base of the subject support.

20. The method of claim 14, wherein the communications network includes a CANopen based network.

21. The method of claim 14, wherein the communications network includes an EtherCAT based network.

22. An imaging system, comprising:
a stationary gantry;
a rotating gantry, rotatably supported by he stationary gantry, and configured to rotate about an examination region about a z-axis;
a radiation source, configured to emit ionizing radiation and supported by the rotating gantry;
a detector array, configured to detect the ionizing radiation and generate projection data indicative thereof;
a subject support, including:
a base configured to vertically translated along a y-axis; and
a tabletop, slideably affixed to the base, and configured to horizontally translate along the z-axis into and out of the examination region;
a communications network including a bus extended through a slip ring which is shared by the rotating gantry and the subject support; and
a master motion controller configured to control rotational motion of the rotating gantry and translational motion of the subject support over the bus of the communications network.

* * * * *